United States Patent [19]

Fisher et al.

[11] Patent Number: 4,876,260

[45] Date of Patent: Oct. 24, 1989

[54] OXATHIOLANES

[75] Inventors: Abraham Fisher, Holon; Ishai Karton, Ness-Ziona, both of Israel

[73] Assignee: State of Israel, Israel Institute of Biological Research, Israel

[21] Appl. No.: 189,210

[22] Filed: May 2, 1988

Related U.S. Application Data

[63] Continuation-in-part of Ser. No. 114,473, Oct. 28, 1987, abandoned.

[51] Int. Cl.$^4$ .................. A61K 31/395; C07D 497/20
[52] U.S. Cl. ...................................... 514/278; 546/18; 546/19
[58] Field of Search ...................... 346/18, 19; 514/278

[56] References Cited

U.S. PATENT DOCUMENTS

| | | | |
|---|---|---|---|
| 4,083,985 | 4/1978 | Cohen et al. | 546/14 |
| 4,104,397 | 8/1978 | Cohen et al. | 546/18 |

FOREIGN PATENT DOCUMENTS

| | | | |
|---|---|---|---|
| 2146962 | 3/1973 | France | 546/18 |
| 2331343 | 6/1977 | France | 546/18 |

*Primary Examiner*—Robert T. Bond
*Attorney, Agent, or Firm*—Sheldon & Mak

[57] ABSTRACT

The present invention accordingly provides in one aspect, novel spiro-oxathiolane/quinuclidine compounds corresponding with the schematic structural formula (I)

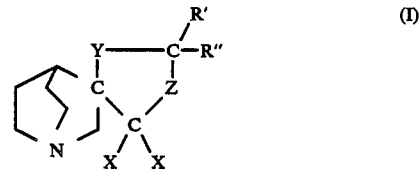

and geometrical isomers, enantiomers, diastereoisomers, racemates and acid addition salts thereof, wherein one of Y and Z is O and the other is $S(=O)_n$; n is 0, 1 or 2; R' and R" are each selected from the group consisting of hydrogen, alkyl, alkenyl, alkynyl, hydroxyalkyl, aminoalkyl, $C_{3-7}$ cycloalkyl, aryl, diarylmethylol, and alkyl substituted by at least one aryl group, provided that at least R' and R" is other than hydrogen; and each X is hydrogen, or when Y is O and Z is $S(=O)_n$ simultaneously, then each X may also be selected from the group consisting of deuterium and tritium, and provided further that when each X is hydrogen, Y is O and Z is S simultaneously, then at least one of R' and R" is selected from the group consisting of alkenyl, alkynyl, cyclopropyl, cyclobutyl, cycloheptyl, hydroxyalkyl and aminoalkyl.

43 Claims, No Drawings

OXATHIOLANES

The present application is a continuation-in-part of application Ser. No. 114,473 filed Oct. 28, 1987, and now abandoned.

FIELD OF THE INVENTION

The present invention relates to new oxathiolane derivatives, to pharmaceutical compositions comprising them and to a method for treating diseases of the central nervous system.

BACKGROUND OF THE INVENTION

The present applicants were co-inventors of previous patent applications relating to novel spiro-oxathiolane/-quinuclidine compounds, see e.g. European patent application No. 0205247 A2, published Dec. 17, 1986, based on Israel patent applications Nos. 75166 dated May 10, 1985 and 77568 dated Jan. 10, 1986, and commonly assigned U.S. patent application Ser. No. 853,404 filed Apr. 18, 1986, the contents of which are incorporated herein by reference. These novel compounds were found to possess central nervous system activity. The biological activity of the compound 2-methyl-spiro(1,3-oxathiolane-5',3)quinuclidine, which exists as geometrical cis-and trans-isomers depending upon whether the 2-methyl group is located on the same side of the oxathiolane ring as the quinuclidine ring nitrogen atom (cis) or on the other side of the quinuclidine ring nitrogen atom (trans), was in particular extensively investigated, and it was found on the basis of preclinical tests that the cis- compound could be especially promising for the control of senile dementia of Alzheimer's type (SDAT).

It is a principal object of the invention to provide novel spiro-oxathiolane/quinuclidine compounds, which bear a close structural relationship to the compounds disclosed and claimed in the aforementioned prior patent applications, but which are nevertheless clearly distinguished therefrom. Further objects of the invention, and especially those which relate to the provision of useful pharmaceutical compositions and methods for the treatment of disease in mammals, will be apparent from the description which follows.

SUMMARY OF THE INVENTION

The present invention accordingly provides in one aspect, novel spiro-oxathiolane/quinuclidine compounds corresponding with the schematic structural formula (I)

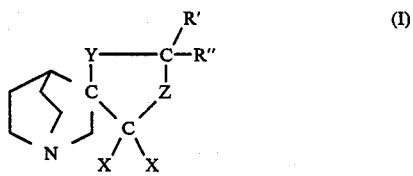

and geometrical isomers, enantiomers, diastereoisomers, racemates and acid addition salts thereof, wherein one of Y and Z is O and the other is $S(=O)_n$; n is 0, 1 or 2; R' and R" are each selected from the group consisting of hydrogen, alkyl, alkenyl, alkynyl, hydroxyalkyl, aminoalkyl, $C_{3-7}$ cycloalkyl, aryl, diarylmethylol, and alkyl substituted by at least one aryl group, provided that at least R' or R" is other than hydrogen; and each X is hydrogen, or when Y is O and Z is $S(=O)_n$ simultaneously, then each X may also be selected from the group consisting of deuterium and tritium, and provided further that when each X is hydrogen, Y is O and Z is S simultaneously, then at least one of R' and R" is selected from the group consisting of alkenyl, alkynyl, cyclopropyl, cyclobutyl, cycloheptyl, hydroxyalkyl and aminoalkyl.

In another aspect, the invention provides a pharmaceutical composition which comprises at least one member of the group of compounds within the definition of the preceding paragraph, in combination with an inert diluent or carrier, the acid addition salts being in this case pharmaceutically compatible acid addition salts.

In yet a further aspect, the invention provides a method for treating diseases of the central nervous system, the particulars of which will be explained (inter alia) in the detailed description which follows.

DETAILED DESCRIPTION OF THE INVENTION

According to a particular embodiment of the compounds of formula (I), X is H, Y is O and Z is $S(=O)_n$; n is 0, 1 or 2; R' and R" are each selected from the group consisting of hydrogen, alkyl, alkenyl, alkynyl, hydroxyalkyl, aminoalkyl, $C_{3-7}$ cycloalkyl, aryl, diarylmethylol, and alkyl substituted by at least one aryl group, provided that at least R' or R" is other than hydrogen, and that when Z is S, then at least one of R' and R" is selected from the group consisting of alkenyl, alkynyl, cyclopropyl, cyclobutyl, cycloheptyl, hydroxyalkyl and aminoalkyl. For convenience, the compounds of this embodiment of the invention will be referred to as compounds (Ia). It will be appreciated that compounds (Ia) in which Z is S (i.e. n is 0) are analogues of the compounds described and claimed in the prior patent applications mentioned above, but in which the values of R' and R" are different. These compounds can therefore be prepared by procedures analogous to those described in the prior applications. It is of course within the competence of a person skilled in the art, where necessary, to protect the hydroxy and amino groups in starting materials containing the said hydroxyalkyl and aminoalkyl moieties and to regenerate these groups in order to obtain the desired products. Compounds (Ia) in which Z is not S (i.e. where n is 1 or 2) may be prepared, for example, by oxidation of the compounds where Z is S, e.g. with $H_2O_2$. It is moreover to be noted that compounds (Ia), when n is 1, i.e. the sulfoxides, exist as cis- and trans-isomers in their own right, in other words each of the unoxidized cis- and trans-spiro compounds (Ia, n=0) gives rise to two distinct geometrical isomeric sulfoxides. In this context, the term "trans-sulfoxide" means a compound of the present invention in which the sulfoxide moiety is trans- with respect to the nitrogen atom of the quinuclidine ring.

According to a further particular embodiment of the compounds of formula (I), X is selected from the group consisting of deuterium and tritium, Y is O and Z is $S(=O)_n$; n is 0, 1 or 2; and R' and R" are each selected from the group consisting of hydrogen, alkyl, alkenyl, alkynyl, hydroxyalkyl, aminoalkyl, $C_{3-7}$ cycloalkyl, aryl, diarylmethylol, and alkyl substituted by at least one aryl group, provided that at least R' or R" is other than hydrogen. Compounds according to this particular embodiment of the invention will be conveniently denoted compounds (Ib).

Compounds (Ib) may be prepared, in brief, by a 3-step process. The first step comprises oxidation of the spiro compounds of the aforementioned prior applications, or of those compounds (Ia), above, where Z is S, to the corresponding sulfoxides or sulfones. In the second step, the sulfoxides or sulfones are labelled with deuterium or tritium, and in the third step the labelled-sulfoxides or -sulfones are reduced to give the compounds (Ib), where Z is S.

It is of interest that when the non-oxidized spiro compounds, in which one of R' and R" is a substituent and the other of which is a hydrogen atom, are submitted to the 3-step process just described, it might have been expected that isotope-substitution would have occurred at position 2 rather than position 4, owing to the anticipated activation of the hydrogen atom in this position both by the sulfone or sulfoxide moiety and by the adjacent oxygen atom (c.f. the activation of the hydrogen atoms attached to α-carbon in ethers, for example), whereas the hydrogen atoms in position 4 would be activated only by the sulfone or sulfoxide moiety. However, the inventors made the surprising discovery that both hydrogen atoms in the 4-position in such starting materials were susceptible to substitution by deuterium or tritium, in preference to the hydrogen atom in the 2-position. It would seem possible, therefore, that steric factors play a part in preventing isotope replacement in position 2 in the starting materials.

It should be noted additionally that in the starting materials for the 3-step process, in which one of R' and R" is a substituent and the other of which is a hydrogen atom, the 2-carbon atom will be asymmetric, so that in this instance the said process may be carried out with a starting material which is enriched in respect of a particular stereoisomer.

A preferred starting material of the type just referred to, for use in the 3-step process, is 2-methylspiro(1,3-oxathiolan-5,3') quinuclidine (II), and the obtained end-products in this instance will be the 4-dideutero and 4-ditritio derivatives. Particularly preferred is such a starting material which has been enriched in a form selected from the (±)-, (+)-and (−)-cis-isomers and the (±)-, (+)- and (−)-trans-isomers, e.g. which is at least about 95% enriched. Such a compound which has been enriched in the (±)-cis- or -trans isomers is described in the above-mentioned European patent application No. 0205247, as well as in Israel patent application No. 81652 (04627), the contents of which are incorporated herein by reference. The (±)-and (−)-cis-isomers and the (+)- and (−)-trans-isomers of (II) are described and claimed in our copening U.S. patent application Ser. No. 084,799, as filed Aug. 13, 1987.

At this point it should be emphasized, that in contrast to the usual prior art methodology for placing a deuterium or tritium atom in a particular position of a molecular structure, which requires an unambiguous (and generally multi-step) synthetic route, the 3-step process affords a relatively simple manner of achieving the same object. The advantage is of course especially pronounced where particular steroisomeric forms are concerned, insofar as previously separated stereoisomeric forms may be used directly as starting materials, and any separation of stereoisomers at the end of a tedious synthetic process is avoided. Confirmation that deuterium or tritium have in fact been placed in the desired positions can of course be checked by physical measurement, as is well-known.

As will be appreciated by those skilled in the art, the individual steps of the 3-step process of the invention, taken separately, and comprising the operations of oxidation, isotope replacement and reduction, are known per se. It is accordingly within the scope of this process to use any relevant known methods for the oxidation of thioethers to sulfoxides and sulfones, for the replacement of hydrogen atoms by deuterium or tritium atoms, and for the reduction of the labelled sulfoxides or sulfones back to the thioethers.

As examples only of reagents which may be used for these steps, there may be mentioned effecting the oxidation step by means of hydrogen peroxide, the isotopic replacement step by means of $D_2O$ or $H_2O$ under alkaline conditions, and the reduction step by means of a complex hydride or a dithionite.

In the preceding description, particular emphasis has been placed on the utilization of starting materials for the 3-step process in which the 2-carbon atom is mono-substituted. However, it will be evident that such a process may also be effected starting with the non-oxidized spiro compounds in which the 2-carbon atom is disubstituted, in which case the isotope substitution will of course normally be effected at that other (unsubstituted) carbon atom. The process may of course be effected on such a starting material which is enriched in respect of a particular stereoisomeric form thereof (e.g. a geometrical isomer, an enantiomer, a diastereoisomer or a racemate), and especially such a starting material which is at least about 95% enriched.

Also, as has already been noted in the case of sulfoxides (Ia), so too the corresponding compounds (Ib, n=1), i.e. the sulfoxides, exist as cis- and trans-isomers in their own right, in other words each of the unoxidized cis- and trans-spiro compounds (Ib, n=0) gives rise to two distinct geometrical isomeric sulfoxides.

In yet a further embodiment of the compounds of formula (I), X is H, Z is O and Y is $S(=O)_n$; n is 0, 1 or 2; and R' and R" are each selected from the group consisting of hydrogen, alkyl, alkenyl, alkynyl, hydroxyalkyl, aminoalkyl, $C_{3-7}$ cycloalkyl, aryl, diarylmethylol, and alkyl substituted by at least one aryl group, provided that at least R' or R" is other than hydrogen. These compounds will be denoted (Ic).

Compounds (Ic, n=0) may be prepared by reacting the thioepoxide of 3-methylenequinuclidine with a carbonyl compound of formula R'R"CO. The desired thioepoxide, which is believed to be a novel compound, may in turn be prepared by reacting the corresponding epoxide with a thiocyanate, such as KCNS. The overall reaction may be represented as follows:

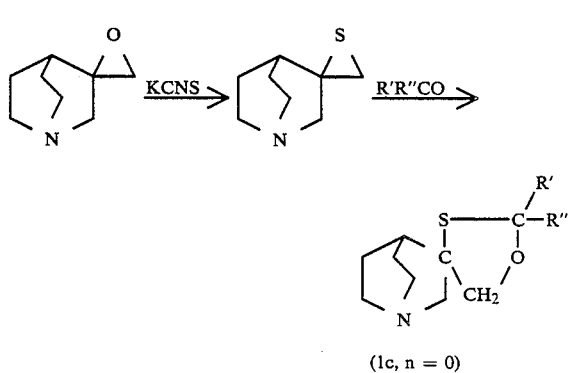

(Ic, n = 0)

A presently preferred example of (Ic, n=0) is 2-methyl-spiro(1,3-oxathilan-4,3')quinuclidine. Compounds (Ic, n=1 or 2) may be prepared from the unoxidized analogues (n=0), by oxidation with e.g. $H_2O_2$. As has already been noted in the case of sulfoxides (Ia) and (Ib), so too the corresponding compounds (Ic, n=1), i.e. the sulfoxides, exist as cis- and trans-isomers in their own right, in other words each of the unoxidized cis-and trans-spiro compounds (Ic, n=0) gives rise to two distinet geometrical isomeric sulfoxides.

Thus, a group of presently preferred compounds of formula (I) are: 2-methylspiro(1,3-oxathiolan-5,3')quinuclidine-3-oxide, 2-methylspiro(1,3-oxathiolan-5,3')quinuclidine-3,3-dioxide, 4,4-dideutero-2-methylspiro(1,3-oxathiolan-5,3')quinuclidine-3-oxide, 4,4-ditritio-2-methylspiro(1,3-oxathiolan-5,3')quinuclidine-3-oxide, 4,4-dideutero-2-methylspiro(1,3-oxathiolan-5,3')quinuclidine, 4,4-ditritio-2-methylspiro(1,3-oxathiolan-5,3')quinuclidine and 2-methylspiro(1,3-oxathiolan-4,3')quinuclidine, and more particularly the following, namely: cis-2-methylspiro(1,3-oxathiolan-5,3')quinuclidine-cis-3-oxide, cis-2-methylspiro(1,3-oxathiolan-5,3')quinuclidine-trans-3-oxide, trans-2-methylspiro(1,3-oxathiolan-5,3')quinuclidine-cis-3-oxide, trans-2-methylspiro(1,3-oxathiolan-5,3')quinuclidine-trans-3-oxide, cis-2-methylspiro(1,3-oxathiolan-5,3')quinuclidine-3,3-dioxide, trans-2-methylspiro(1,3-oxathiolan-5,3')quinuclidine-3,3-dioxide, cis-4,4-dideutero-2-methylspiro(1,3-oxathiolan-5,3')quinuclidine-trans-3-oxide, cis-4,4-ditritio-2-methylspiro(1,3-oxathiolan-5,3')quinuclidine-trans-3-oxide, cis-4,4-dideutero-2-methylspiro(1,3-oxathiolan-5,3')quinuclidine, and cis-4,4-ditritio-2-methylspiro(1,3oxathiolan-5,3')quinuclidine, and enantiomers, diastereoisomers, racemates and acid addition salts thereof, and (+)-cis-2-methylspiro(1,3-oxathiolan-4,3')quinuclidine, (+)-trans-2-methylspiro(1,3-oxathiolan-4,3')quinuclidine, (−)-cis-2-methylspiro(1,3-oxathiolan-4,3')quinuclidine, (−)-trans-2-methylspiro(1,3-oxathiolan-4,3')quinuclidine, (±)-cis-2-methylspiro(1,3-oxathiolan-4,3')quinuclidine and (±)-trans-2-methylspiro(1,3-oxathiolan-4,3')quinuclidine, and acid addition salts thereof.

At least those compounds of the present invention where one of R' and R" is methyl and the other is a hydrogen atom are in general muscarinic agonists with a high specificity for the central nervous system. They are highly specific for a subpopulation of muscarinic receptors, namely pirenzepine-sensitive M1 receptors. Due to their pharmacological properties, these compounds can activate central cholinergic functions under conditions where the cholinergic system is hypofunctional. These compounds can therefore be utilized for the treatment of conditions such as presenile dementia, senile dementia of Alzheimer's type (SDAT), mixed Alzheimer's and Parkinson's disease, tardive dyskinesia, acute confusion conditions, hyperkinesia, mania, Pick's disease, Huntington's chorea, Friedrich's ataxia, Down's syndrome, Gilles de la Tourette disease, post encephalitic amnesic syndrome, alcohol withdrawal symptoms, and progressive supranuclear palsy, because all of these disease states are disturbances in which a central cholinergic hypofunction has been implicated at least to a certain extent.

Certain compounds of the invention, and especially those in which one of R' and R" is methyl and the other is a hydrogen atom, would appear to be of value for the treatment of SDAT. Thus, in SDAT patients, such compounds could be used in combination with anticholinesterase inhibitors such as physostigmine or tetrahydroaminoacridine; in combination with acetylcholine precursors such as choline or lecithin; in addition to "nootropic" drugs such as piracetam, aniracetam, oxiracetam or pramiracetam; in addition to compounds that interact with $Ca^{2+}$ channels such as 4-aminopyridine or 3,4-diaminopyridine; or in addition to peptides that can have modulatory effects on acetylcholine release, such as somatostatin; in combination with a peripheral antimuscarinic agent (such as pirenzepine, N-methylatropine or N-butylscopolamine) to counteract peripheral adverse effects that might be expected at high doses, such as salivation, diarrhea, gastric secretion or vomiting, or in combination with transdermal scopolamine such as Scopoderm$^R$ to counteract nausea and/or vomiting; in combination with an adrenergic agonist (clonidine or quanfamicine) in order to alleviate both the cognitive and other impairments associated with a mixed cholinergic-noradrenergic deficiency in SDAT; in combination with Nerve Growth Factor (NGF, which is administered either by a nasal spray or intracerebroventicularly).

The compounds of the present invention, with or without the aforementioned other active substances, can be administered for example, by way of injection in a suitable diluent or carrier, per os, rectally in the form of suppositories, by way of insufflation or nasal spray, by infusion or transdermally in a suitable vehicle with or without physostigmine or tetrahydroaminoacridine, for example by using the device which is the subject of Israel patent application No. 72684 (vide infra). These compounds might also be used in disturbances where cholinergic underactivity is induced by drugs.

The present compounds, especially where one of R' and R" is methyl and the other is a hydrogen atom, are also of potential use for the treatment of disorders requiring the application of a long-lasting cholinergic agent of mild local activity. Such an agent is needed in disorders such as glaucoma, as the compound is not destroyed by the enzyme which deactivates acetylcholine, i.e. acetyl- and butyryl-cholinesterase, and may also be used for the treatment of peripheral cholinergic disorders such as myasthenia gravis, urinary bladder dysfunctions, Adi's disease and Eaton-Lambret disease.

The present compounds form stable addition salts with organic and inorganic acids. While for therapeutic purposes such salts should be pharmaceutically compatible, nevertheless it may be convenient, as for example for the purpose of isolation, to employ acid addition salts which are not pharmaceutically compatible, and the invention includes also the latter kind of acid addition salts. As will be obvious to those skilled in the art, the free bases may be converted to acid addition salts by reaction with the appropriate acid, and the salts may be converted by reaction with a base (e.g., an alkali metal hydroxide in aqueous solution) to the corresponding free bases.

In the pharmaceutical composition aspect of the present invention, such composition may comprise at least one member of the group consisting of the spiro-oxathiolane/quinuclidine compounds corresponding with the schematic structural formula (I), as set forth generally or particularly hereinabove, and including geometrical isomers, enantiomers, diastereoisomers and racemates thereof, and pharmaceutically compatible acid addition salts thereof, together with an inert carrier or diluent. The term "pharmaceutical composition" is to be construed widely, insofar as it includes such composition for diagnostic purposes which may comprise the tritium-containing compounds of the invention, as well as such composition for therapeutic purposes which may comprise the non-radioactive compounds of the invention.

The term "pharmaceutically compatible acid addition salts" as used herein refers to combinations of the present compounds with relatively non-toxic inorganic or organic acids. Illustrative only of suitable acids are sulfuric, phosphoric, hydrochloric, hydrobromic, hydriodic, sulfamic, methanesulfonic, benzenesulfonic, para-toluenesulfonic, acetic, lactic, succinic, maleic, tartaric, citric, gluconic, ascorbic, benzoic and cinnamic acids.

Where the term "pharmaceutical composition" is used in the present specification and claims, this is to be understood in the sense that it may be suitable for human and/or veterinary treatment. In the pharmaceutical compositions of the invention, suitable pharmaceutical carriers and diluents, which comprise both solids and liquids, may, by way of example only, be selected from corn starch, lactose, calcium phosphate, stearic acid, polyethylene glycol, water, sesame seed oil, peanut oil, propylene glycol, and so forth. This composition may be in a form suitable for oral, rectal or parenteral administration, or for administration by insufflation or nasal spray, or in particular it may be in a form suitable for transdermal administration, and in any event the composition may be in unit dosage form. Exemplary compositions may take the form of tablets, powder, granules, capsules, suspensions, solutions, suppositories, elixirs, ointments and the like.

When the pharmaceutical composition is to be administered transdermally, it is preferred to utilize the drug delivery system according to Israel patent application No. 72684, although transdermal administration in accordance with the invention is not of course limited to this system. Thus, as mentioned previously, the pharmaceutical compositions of the invention adapted for transdermal administration may comprise as an additional ingredient, a low molecular weight fatty acid.

The pharmaceutical compositions of the present invention may alternatively comprise: (a) at least one member of the group consisting of spiro-oxathiolane/quinuclidine compounds corresponding with the schematic structural formula (I) as depicted hereinbefore, and geometrical isomers, enantiomers, diastereoisomers and racemates thereof, wherein one of Y and Z is O and the other is $S(=O)_n$; n is 0, 1 or 2; R' and R" are each selected from the group consisting of hydrogen, alkyl, alkenyl, alkynyl, hydroxyalkyl, aminoalkyl, $C_{3-7}$ cycloalkyl, aryl, diarylmethylol, and alkyl substituted by at least one aryl group, provided that at least R' or R" is other than hydrogen; and each X is hydrogen, or when Y is O and Z is $S(=O)_n$ simultaneously, then each X may also be selected from the group consisting of deuterium and tritium, and (for reasons noted previously) (b) at least one compound selected from the group consisting of physostigmine, tetrahydroaminoacridine, choline, lecithin, piracetam, aniracetam, pramiracetam, oxiracetam, 4-aminopyridine, 3,4-diaminopyridine, somatostatin, pirenzepine, N-methylatropine, N-butylscopolamine, scopolamine, clonidine, quanfamicine and Nerve Growth Factor, and provided further that when each X is hydrogen, Y is O and Z is S simultaneously, then either in component (a) at least one of R' and R" is selected from the group consisting of alkenyl, alkynyl, cyclopropyl, cyclobutyl, cycloheptyl, hydroxyalkyl and aminoalkyl, or component (b) comprises at least one compound selected from the group consisting of pirenzepine, N-methylatropine, N-butylscopolamine, scopolamine, clonidine, quanfamicine and Nerve Growth Factor.

As has already been indicated, the present invention provides in another aspect, a method for treating diseases of the central nervous system in mammals (especially diseases due to a deficiency in the central cholinergic system), which comprises administering to the mammal, preferably in the form of a pharmaceutical composition as described above, at least one member of the group consisting of spiro-oxathiolane/quinuclidine compounds corresponding with the schematic structural formula (I) as depicted in claim 1, and geometrical isomers, enantiomers, diastereoisomers and racemates thereof, wherein one of Y and Z is O and the other is $S(=O)_n$; n is 0, 1 or 2; R' and R" are each selected from the group consisting of hydrogen, alkyl, alkenyl, alkynyl, hydroxyalkyl, aminoalkyl, $C_{3-7}$ cycloalkyl, aryl, diarylmethylol, and alkyl substituted by at least one aryl group, provided that at least R' or R" is other than hydrogen; and each X is hydrogen, or when Y is O and Z is $S(=O)_n$ simultaneously, then each X may also be deuterium, and provided further that when each X is hydrogen, Y is O and Z is S simultaneously, then at least one of R' and R" is selected from the group consisting of alkenyl, alkynyl, cyclopropyl, cyclobutyl, cycloheptyl, hydroxyalkyl and aminoalkyl, and pharmaceutically compatible acid addition salts thereof.

In an alternative embodiment of this aspect of the invention, there is also coadministered with the said at least one member, at least one compound selected from the group consisting of physostigmine, tetrahydroaminoacridine, choline, lecithin, piracetam, aniracetam, pramiracetam, oxiracetam, 4-aminopyridine, 3,4-diaminopyridine, somatostatin, pirenzepine, N-methylatropine, N-butylscopolamine, scopolamine, clonidine, quanfamicine and Nerve Growth Factor, provided additionally that when said at least one compound is selected from the group consisting of pirenzepine, N-methylatropine, N-butylscopolamine, scopolamine, clonidine, quanfamicine and Nerve Growth Factor, then the restriction that when each X is hydrogen, Y is O and Z is S simultaneously, at least one of R' and R" is necessarily selected from the group consisting of alkenyl, alkynyl, cyclopropyl, cyclobutyl, cycloheptyl, hydroxyalkyl and aminoalkyl, does not apply.

When according to this aspect of the invention, senile dementia of Alzheimer's type is treated, then in the method which comprises administering to a patient at least one member of the group of compounds described, or a pharmaceutically of a pharmaceutical composition, as described above, the compounds of formula (I) may be administered via the oral route in an amount which lies within the range of about 0.1 to about 60 mg./kg., preferably about 0.1 to about 10 mg./kg. body weight, more preferably about 1 to about 5 mg./kg. body weight. On the other hand, the compounds may be administered via the parenteral route (which includes, for example, intramuscular, intravenous and subcutaneous administration) in an amount which lies within the range of about 0.01 to about 10 mg./kg., preferably about 0.05 to about 5 mg./kg. body weight, more preferably about 0.1 to about 2 mg./kg. body weight.

In prescribing a particular form and rate of administration, the physician will of course take into consideration the usual factors such as the severity of the symptoms, the physical circumstances of the patient, and so forth.

Taking into account the usual weight ranges of patients, the foregoing dosage ranges, and the possibility that it may be desirable to administer multiple rather than single doses, pharmaceutical compositions in accordance with the invention which are adapted for oral or parenteral administration, may contain the active ingredient in an amount (for example) in the range of about 0.5 to about 100 mg., preferably about 5 to about 100 mg., more preferably in the range of about 10 to about 50 mg.

For the purpose of definition, it is intended that the expression "method for the treatment of diseases of the central nervous system", and like expressions, throughout the specification and claims, be taken to include a method for the prevention of drug-induced diseases of the central nervous system.

The invention will be illustrated by the following non-limitative Examples.

EXAMPLE 1

Preparation of sulfoxides and a sulfone from 2-methylspiro(1,3-oxathiolan-5,3')quinuclidine (II)

(a) ($\pm$)-cis-(II).HCl (18.9 g., 0.08 mol.) was dissolved in 200 ml. acetic acid and 25 ml. 30% hydrogen peroxide was added at room temperature. The mixture was stirred for 30 minutes, basified with 20% aqueous sodium hydroxide, and extracted with chloroform (3×200 ml.). The chloroform extracts were dried (MgSO$_4$) and evaporated to give 16.2 g. (94% yield) of a white powder which comprised a 1:1 mixture of ($\pm$)-cis-(II)-cis- and -trans-sulfoxides. The crude product (10 g.) was purified by chromatography on 250 g. silica, using 17:13:3:0.4 chloroform/petroleum ether/ethanol/28% aq. NH$_3$, to give 3.7 g. ($\pm$)-cis-(II)-trans-sulfoxide, 3 g. of a mixture of ($\pm$)-cis-(II)-cis-and -trans-sulfoxides and 2.2 g. ($\pm$)-cis-(II)-cis-sulfoxide.

($\pm$)-cis-(II)-trans-sulfoxide:

$^1$H-NMR (CDCl$_3$-TMS) $\delta$=1.7 (d, 3H CH$_3$ ) (J=6.3 Hz); 1.3 –2.1 (m, 5H); 2.56 (d, 1H) (J=14 Hz); 3.34 (d, 1H) (J=14 Hz); 2.6–3.2 (m, 6H); 4.7 (q, 1H) (J=6.3 Hz).

MS: M$\pm$215; base peak m/e 96.

High resolution molecular weight determination—calc. for C$_{10}$H$_{17}$NSO$_2$: 215.0978; found: 215.1055.

$^{13}$C-NMR (CDCl$_3$-TMS) $\delta$=16.5 (CH$_3$); 58.0 (C$_4$); 87.7 (C$_5$); 102.5 (C$_2$).

Cis-(II)-trans-sulfoxide can be used for the same disease states as described for cis-(II) in our published European patent application No. 0205247, and it also appears to be a natural metabolite of cis-(II).

($\pm$)-cis-(II)-cis-sulfoxide:

1H-NMR (CDCl$_3$ -TMS) $\delta$=1.55 (d, 3H CH$_3$) (J=6.3 Hz); 1.3–2 (m, 5H); 2.8 (d, 1H) (J=14 Hz); 3.6 (d, H) (J=14 Hz); 4.58 (q, 1H) (J=6.3 Hz).

MS; M$\pm$215; base peak m/e 96.

High resolution molecular weight determination—calc. for C$_{10}$H$_{17}$NSO$_2$: 215.0978; found: 215.0930.

$^{13}$C-NMR (CDCl$_3$-TMS) $\delta$=12.64 (CH$_3$); 82.3 (C$_4$); 85.6 (C$_5$); 91.7 (C$_2$).

(b) ($\pm$)-trans-(II).HCl was oxidized, and the resultant product was separated, as in part (a), above. The following were isolated.

($\pm$)-trans-(II)-trans-sulfoxide:

$^1$H-NMR (CDCl$_3$-TMS) $\delta$=1.66 (d, 3H CH$_3$) (J=6 Hz); 4.72 (q, 1H) (J=6 Hz).

MS: M$\pm$215; base peak m/e 96.

High resolution molecular weight determination—calc. for C$_{10}$H$_{17}$NSO$_2$: 215.0978; found: 215.0985.

($\pm$)-trans-(II)-cis-sulfoxide:

$^1$H-NMR (CDCl$_3$-TMS) $\delta$=1.63 (d, 3H CH$_3$) (J=6 Hz); 4.65 (q, 1H) (J=6 Hz).

MS: M$\pm$215; base peak m/e 96.

High resolution molecular weight determination—calc. for C$_{10}$H$_{17}$NSO$_2$: 215.0978; found: 215.1013.

(c) ($\pm$)-cis-(II).HCl (20 g., 0.085 mol.) was dissolved in 200 ml. acetic acid and 40 ml. 30% hydrogen peroxide was added and the mixture was stirred overnight at room temperature. It was then basified with 20% aqueous sodium hydroxide, and extracted with chloroform (3×200 ml.). The chloroform extracts were dried (MgSO$_4$) and evaporated, and purified by quantitative HPLC. Packing material: Lichrosorb Si 100 10 $\mu$m. Eluent: 5% v/v methanol in chloroform. 1.3 g. of pure ($\pm$)-cis-(II)-sulfone m.p. 251°–253° C. was obtained.

TLC ammonium hydroxide (25% in water) 2% v/v in methanol on silica Art 5735 (Merck) R$_f$0.52.

$^1$H-NMR (CDCl$_3$-TMS) $\delta$=1.6 (d, 3H CH$_3$) (J=6 Hz);

MS: M$\pm$231; base peak m/e 167.

EXAMPLE 2

Preparation of deuterated ($\pm$)-cis-(II)-trans-sulfoxide ($\pm$)-cis-(II)-trans-sulfoxide (0.9 g., 4.2 mmol.) was dissolved in 3.8 g. D$_2$O and the exchange was performed under basic conditions with sodium hydroxide (0.2 g., 5 mmol.). The reaction mixture was left at 25° C. for 60 hours, extracted with chloroform (2×10 ml.), and the chloroform was dried and evaporated to yield 0.85 g. of pure deuterated sulfoxide.

$^1$H-NMR (CDCl$_3$-TMS) $\delta$=1.7 (d, 3H CH$_3$) (J=6.3 Hz); 4.69 (q, 1H) (J=6.3 Hz).

MS is enclosed M =217; base peak m/e 96.

$^{13}$C-NMR (CDCl$_3$-TMS) $\delta$=16.5 (CH$_3$); 67.6 (C$_5$); 102.5 (C$_2$).

EXAMPLE 3

Preparation of deuterated ($\pm$)-cis-(II)

(a) Deuterated ($\pm$)-cis-(II)-trans-sulfoxide (0.45 g. in 2 g. D$_2$O) was acidified using 4 ml. of 10% hydrochloric acid, and reduced at 50° C. for 1 hour with sodium dithionite (2 g. of 85%). The mixture was cooled, basified and extracted with chloroform (2×10 ml.). The chloroform extracts were dried and evaporated, and the residue was dissolved in 50 ml. hexane and precipitated with hydrogen chloride to give 0.2 g. of pure product in the form of the HCl salt. $^1$H-NMR (CDCl$_3$-TMS) $\delta$=1.57 (d, 3H CH$_3$) (J=6 Hz); 5.15 (q, 1H) (J=6 Hz).

MS is enclosed M$\pm$201; base peak m/e 96.

$^{13}$C-NMR (CDCl$_3$-TMS) $\delta$=22.4 (CH$_3$); 80.4 (C$_2$); 83.9 (C$_5$).

(b) The same starting material (0.9 g.) was reduced with LiAlH$_4$. After work-up a 69% yield of pure title product (isolated as the HCl salt) was obtained.

MS studies based on the data obtained according to Examples 1–3 show addition of two mass units (exchange of two hydrogen atoms by deuterium). The type of fragmentation can be explained by exchange of hydrogen atoms on the five-membered ring. $^{13}$C NMR studies show disappearance of the large C$_4$ resonance and appearance of a multiplet instead, thus indicating that the hydrogen atoms near C$_4$ were substituted by deuterium. $^1$H NMR of the deuterated (II) emphasizes that (a) no isomerization takes place during reaction, and (b) no exchange of hydrogen takes place during the labelling step since the integration ratio between the CH₃ and H remains 3:1.

EXAMPLE 4

Preparation of tritiated (±)-cis-(II)-trans-sulfoxide (±)-cis-(II)-trans-sulfoxide (0.45 g., 2.1 mmol.) was dissolved in 2.2 ml. H₂O (50Ci/ml.). Sodium hydroxide (0.2 g.) was added and the mixture was left at room temperature for 70 hours. The title product as thus formed was used for Example 5 without isolation.

EXAMPLE 5

Preparation of tritiated (±)-cis-(II)

The solution obtained in Example 4 was acidified with 4 g. of 10% aqueous HCl, and 2 g. of 85% sodium dithionite was added. The clear solution was stirred at 50° C. for one hour, cooled and then basified with 3 g. 20% w/w aqueous sodium hydroxide. The mixture was extracted with chloroform (1×20 ml.), the extract was transferred into 200 ml. hexane, 0.7 g. 0.5M HCl in isopropanol was added to pH ∼3 and the precipitate was filtered and dried to give 0.35 g. (1.5 mmol.) of the title product (71% yield) as the HCl salt. Specific activity: 543 mCi/mmole, total activity 823 mCi.

The product was checked by TLC using chloroform-petroleum ether-ethanol-ammonia 17:13:4:0.4 to give one spot $R_f$=0.4 which was detected as a brown spot on exposure to I₂ vapor. Radiochemical purity was determined using the same plate.

The HCl salt was dissolved in water containing 5% ethanol 10 mCi/ml. and kept at 4° C.

Tritiated (±)-cis-(II) and its corresponding isolated enantiomers can be used as radioactive ligands in receptor binding studies, since they would be expected to bind to $M_1$ muscarinic receptors. Such a probe can be utilized both in displacement studies and in autoradiography of $M_1$ receptors in animal and human brain samples taken at autopsy or biopsy. In addition, they can be used in pharmacokinetic studies in experimental animals.

Deuterated (±)-cis-(II) and its corresponding isolated enantiomers can be used as an internal standard in pharmacokinetic studies in experimental animals and can also be used in the disease states described in European Patent Application No. 0205247.

EXAMPLE 6

Preparation of 2-methylspiro(1,3-oxathiolan-4,3')quinuclidine (III), including its geometrical and optical isomers (a) 3-methylenequinuclidine thioepoxide (IV)

In a 1 l. flask fitted with a magnetic stirrer and a thermometer were placed 3-methylenequinuclidine epoxide (60 g., 0.43 mole), potassium thiocyanate (60 g., 0.62 mole) and 500 ml. 1:1 aqueous dioxane. The mixture was heated to 50° C. until the epoxide had completely disappeared (about 3 hours), and then cooled and extracted with toluene. The toluene solution was dried and evaporated to yield the desired product as a colorless oil. M±155. TLC: silica, 2% ammonia in methanol; $R_f$ 0.7.

(b) Compound (III) (1:1 cis-trans, cis and trans)

The thioepoxide (IV) from stage (a) (19 g., 0.12 mole) was placed in a 1 l. three-neck flask fitted with a mechanical stirrer, a thermometer and a dropping funnel. Chloroform (350 ml.) was added and the mixture cooled to −10° C. Acetaldehyde (120 ml.) was added, followed by boron trifluoride etherate (240 ml.). while keeping the temperature at 5°-15° C. The mixture was left overnight at 20° C., poured into ice-water containing sodium hydroxide (200 g.) and extracted with chloroform. The chloroform phase was dried and evaporated, and the resultant oily residue was dissolved in ether and precipitated by addition of oxalic acid. The crude oxalate was basified, and the base subjected to chromatographic separation on a silica gel column (70 -230 mesh, Merck Art #7734) using as eluent 2% aqueous ammonia in methanol). The separate geometrical isomers of (III), coded AF122A and AF122B, were thus separated from the cis-trans mixture and from (by-product) cis-trans (II). product) cis-trans (II). The isomer ratio was followed by gas chromatography [high performance "Carbowax 20M" capillary column 50 m. ×0.2 mm. ×0.2 μm., carrier gas 0.8 ml./min. N₂, oven 160° C. isothermal, detector FID]. Retention time in minutes: (IV) 10; cis-(II) 17.3; trans-(II) 17.9; cis-(III) 18.8; trans-(III) 19.1. MS of each isomer of (III): M±199. Base peak m/e 155. Table 1 shows ¹H-NMR chemical shifts in ppm relative to tetramethylsilane, of the separated isomers (free bases in CDCl₃).

TABLE 1

| Compound | $H_{a,b}$ | $H_c$ | CH₃ |
|---|---|---|---|
| AF122A | 3.50d (J = 9 Hz)<br>4.30d (J = 9Hz) | 5.38 g (J = 6Hz) | 1.53d<br>(J = 6Hz) |
| AF122B | 4.13d (J = 9Hz)<br>3.72d (J = 9Hz) | 5.26 g (J = 6Hz) | 1.58d<br>(J = 6Hz) |

(c) Optical resolution (±)-AF122B as free base (4.1 g., 20.6 mmole) and D-tartaric acid (1.5 g., 10 mmole) were dissolved under reflux in 175 g. 10:1 (v/v) isopropanol/methanol. The solution was allowed to cool to room temperature and left overnight. The resulting precipitate (3.06 g.) was filtered off and recrystallized twice from 10:1 (v/v) isopropanol/methanol. The solid product was basified and reprecipitated as the hydrochloride (1.6 g., 6.8 mmole); it had m.p. 228°-230° C. and $[\alpha]_D^{20}$ ±36±3.5 (free base in ethanol).

The mother liquor was evaporated, basified and treated with L-tartaric acid in the same manner. After two recrystallizations, the resulting tartrate was basified and reprecipitated as the hydrochloride (1.19 g., 5.06 mmole); $[\alpha]_D^{20}$ −33±3 (free base in ethanol).

The following properties apply to each enantiomer. $R_f$ (TLC, 2% v/v aq. ammonium hydroxide (25%) in methanol on Silica Art 5735 (Merck)) 0.5. NMR spectrum using pure 2,2,2-trifluoro-1-(9-anthryl)ethanol (C₆D₆) shows the presence of a signale enantiomer (>90% optical purity). The NMR spectrum of the hydrochloride salt in CDCl₃ is identical to that of the (±)-isomer hydrochloride.

By a similar procedure to the foregoing there were obtained:
(±)-AF122A $[\alpha]_{20}^{20}$ ±6±0.6 (free base in ethanol); and
(−)-AF122A $[\alpha]_D$ −7±1.4 (free base in ethanol).

Compound (III) as the mixture of geometrical isomers, or in the form of either geometrical isomer (including the respective enantiomers) can be used for the same disease states as described for cis-(II) in our prior published European patent application, since its $M_1$ selectivity is preserved even in the mixture of the geometrical isomers.

Biological Testing

The potency of compound (III), and for comparison, other putative cholinergic compounds in displacing from rat brain homogenates (forebrain, frontal cortex or cerebellum) the following $^3$H-labelled compounds, namely, $^3$H-quinuclidinyl benzilate ($^3$H-QNB; a non-selective $M_1$ and $M_2$ antagonist), $^3$H-Pirenzepine ($^3$H-PZ; a selective $M_1$ antagonist) and $^3$H-cis-dioxolane ($^3$H-CD, a non-selective $M_1$ and $M_2$ agonist), is shown in Tables 2A, 2B and 2C. Oxotremorine is mainly an $M_2$ agonist, while McN-A-343 is mainly an $M_1$ agonist.

TABLE 2A

| Compd. tested # | (a) forebrain 3 Ki(H-PZ) μM | (b) forebrain 3 Ki(H-QNB) μM | (c) forebrain 3 Ki(H-CD) μM | (d) a:b | (e) a:c |
|---|---|---|---|---|---|
| 1 | 0.6 ± 0.2 (4) | 2.1 ± 0.3 (8) | 9.6 ± 4.2 (2)* | 0.29 | 625.0 |
| 2 | 5.0 ± 1.7 (4) | 16.9 ± 1.3 (3) | 0.4 ± 0.1 (4) | 0.30 | 12.3 |
| 3 | 14.6 ± 2.9 (4) | 24.7 ± 2.3 (8) | 1.8 ± 0.1 (2) | 0.59 | 8.3 |
| 4 | 1.0 ± 0.4 (8) | 7.0 ± 1.0 (17) | 0.45 ± 0.18 (4) | 0.14 | 2.2 |
| 5 | 1.1 ± 0.3 (3) | 3.7 ± 0.7 (5) | 0.21 ± 0.06 (2) | 0.3 | 5.2 |
| 6 | 9.6 ± 1.8 (3) | 47.4 ± 13.7 (5) | 7.5 (1) | 0.20 | 1.3 |
| 7 | 1.22 ± 0.4 (2) | 7.0 ± 0.5 (2) | NT | 0.17 | |

TABLE 2B

| Compd. tested # | (a') frontal cortex 3 Ki(H-PZ) μM | (b') frontal cortex 3 Ki(H-QNB) μM | (c') frontal cortex 3 Ki(H-CD) μM | (f) a':b' | (g) a':c' |
|---|---|---|---|---|---|
| 1 | 0.22 ± 0.07 (2) | 2.2 ± 0.3 (4) | 0.0016 ± 0.0004 (2) | 0.1 | 137.5 |
| 2 | | 7.9 ± 1.0 (3) | | | |
| 4 | 0.96 ± 0.05 | 7.1 ± 1.5 (7) | 0.39 ± 0.21 (1) | 0.13 | 2.5 |
| 5 | 0.41 ± 0.08 (3) | NT | 0.20 ± 0.04 (2) | | 2.1 |
| 6 | 4.63 ± 0.42 (3) | NT | 7.94* (1) | | 0.6 |
| 8 | 1.66 ± 0.24 (2) | 15.3 ± 2.2 (5) | 2.30 (1) | 0.11 | 0.7 |
| 9 | 12.1 (1) | | | | |
| 10 | 7.4 (1) | | | | |
| 11 | 0.84 ± 0.03 (2) | 9.7 ± 2.3 (4) | 0.75* (1) | 0.09 | 1.0 |
| 12 | 0.35 ± 0.04 (2) | | | | |
| 13 | 4.21 ± 0.47 (3) | | | | |
| 14 | 5.5 ± 0.43 (2) | 34.1 ± 3.0 (2) | 3.06 ± 2 (2) | 0.18 | 1.8 |

*forebrain

TABLE 2C

| Compd. tested # | (b") cerebellum 3 Ki(H-QNB) μM | (h) a:b" | (i) a':b" | (j) b:b" | (k) b':b" |
|---|---|---|---|---|---|
| 1 | 0.7 ± 0.3 (3) | 0.86 | | 3.00 | |
| 1 | 1.31 ± 0.3 (4) | | | | 1.69 |
| 2 | 24.4 ± 4.4 (4) | 0.09 | | 0.31 | 0.32 |
| 3 | 28.0 ± 2.9 (3) | 0.52 | | 0.88 | |
| 4 | 14.8 ± 2.9 (6) | 0.07 | | 0.47 | |
| 4 | 18.1 ± 6.8 (5) | | 0.1 | | 0.39 |
| 5 | 7.9 ± 0.9 (3) | 0.14 | | 0.47 | |
| 6 | 99.2 ± 26.8 (3) | 0.1 | | 0.48 | |
| 8 | 21.1 ± 7.6 (2) | | | | 0.73 |
| 11 | 19.8 ± 6.1 (2) | | | | 0.49 |
| 14 | 44.1 ± 6.5 (2) | | 2.6 | | 0.77 |

Key to Tables 2A, 2B and 2C:
Ki = IC$_{50}$ + (1 + C/K$_D$), where C is the concentration of the radioactive ligand and K$_D$ is the dissociation constant thereof
compounds tested
1 = Oxotremorine (*in M × 10$^{-10}$)
2 = McN-A-343
3 = (±)-trans-(II)
4 = (±)-cis-(II)

TABLE 2C-continued

| #5 = (−)-cis-(II) | #12 = (−)-(III) [(−)-AF122A] |
|---|---|
| #6 = (+)-cis-(II) | #13 = (+)-(III) [(+)-AF122A] |
| #7 = cis-trans-(III) | #14 = (±)-cis-(II)-sulfone |

(NT = not tested)

Discussion of Tables 2A, 2B and 2C. From these Tables, it is evident that compounds #4–#8, #11 and #14 show a high $M_1$ selectivity. Compound #5 is 2.2 times more potent in H-QNB displacement than its racemate (#4). Moreover, the latter is the most selective $M_1$ agonist, being more selective than the prototype $M_1$ agonist McN-A-343. As can be seen from the ratios Ki($^3$H-PZ):Ki($^3$H-CD) and Ki($^3$H-PZ):Ki($^3$H-QNB) in columns (d) and (e) of Table 2A, the structurally rigid spiro oxathiolane/quinuclidines showed higher selectivity towards $M_1$ receptors than McN-A-343 or Oxotremorine. However, there were some apparent discrepancies between the order of the ratios Ki($^3$H-PZ):Ki($^3$H-CD) and Ki($^3$H-PZ):Ki($^3$H-QNB) among the tested compounds, especially in regard to Oxotremorine, compound #3 and McN-A-343. While the order of the ratios Ki($^3$H-PZ):Ki($^3$H-CD) for these three compounds was oxotremorine > McN-A-343 > compound #3, the order of the ratios Ki($^3$H-PZ):Ki($^3$H-QNB) was McN-A-343 > compound #3 > oxotremorine. These ratios are indices for the relative selectivity of the tested compounds towards $M_1$ as against $M_2$ receptors. It is not clear why in one test, oxotremorine showed the weakest relative affinity towards $M_1$ binding sites [Ki($^3$H-PZ):Ki($^3$H-CD)] whereas in the other test its relative affinity towards the $M_1$ binding sites was relatively stronger than McN-A-343 and compound #3 [Ki($^3$H-PZ):Ki($^3$H-QNB)]. One explanation of this phenomenon is that since the affinity of oxotremorine towards all muscarinic receptors is greater than those of the weaker agonists McN-A-343 or compound #3 [Watson et al, JPET 237: 411–418 (1986)], then lower concentrations of oxotremorine are needed to displace both $^3$H-PZ and $^3$H-QNB from forebrain homogenate, especially $^3$H-PZ which possesses lower affinity towards muscarinic receptors than $^3$H-QNB. Thus, in principle, strong agonists will yield a lower Ki($^3$H-PZ):Ki($^3$H-QNB) ratio than weak agonists, without taking into consideration the selectivity of the selected ligands. On the other hand, the K$_D$ of $^3$H-PZ is similar to that of $^3$H-CD and therefore weak and strong agonists should behave similarly in displacing these labelled ligands, unless their selectivity

8 = (±)-(III) (AF122B)
9 = (−)-(III) [(−)-AF122B]
10 = (+)-(III) [(+)-AF122B]
11 = (±)-(III) (AF122A)

towards one receptor subpopulation is different. Therefore, the ratio $K_i(^3H\text{-PZ}):K_i(^3H\text{-CD})$ should represent more accurately the relative affinities towards $M_1$ receptors. Indeed, the order of these ratios for the compounds tested is consistent with the order found for the ratios $IC_{50}(FB):IC_{50}(CER)$ or $IC_{50}$(frontal cortex):$IC_{50}(CER)$, which also serve as indices for $M_1$ versus $M_2$ selectivity, namely, compound #4>compound #3>oxotremorine (FB=forebrain, which contains mainly $M_1$ receptors; CER=cerebellum, which contains mainly $M_2$ receptors).

Also, $(\pm)$-cis-(II)-sulfone, while losing some of its potency, still preserved an outstanding profile as judged by its $M_1$ selectivity (ratio a':c'). Compounds (III) show a $K_i$ value for the displacement of $^3H$-PZ similar to that of $(\pm)$-cis-(II). Since their $K_i$ values for the displacement of $^3H$-QNB are significantly higher than that of $(\pm)$-cis-(II), these compounds may be even more selective than $(\pm)$-cis-(II) in binding to $M_1$ receptors.

Table 3 shows the results of a study of the activity of compounds of the invention on isolated guinea-pig ileum. From this Table, it appears that compounds (III) were not so effective in contracting the guinea pig ileum preparation. In fact, AF122A did not produce any significant contractions in the concentration range within which it binds to the brain receptors and even perturbed the ACh-induced contractions when applied in relatively high concentrations. On the other hand, AF122B contracted the ileum muscle but the contractions were only partially blocked by atropine. The active enantiomer was (+)-AF122B, while (−)-AF122B produced inconsistent contractile response: sometimes at high concentrations it induced contractions, whereas at other times it did not. This inconsistent response might be related to the phenomenon of desensitization that was observed with AF122B. However, AF122B consistently blocked ACh-induced contractions. The absence of the response of the ileum in presence of compounds of the AF122A series, on the one hand, and the high affinity of these compounds towards brain muscarinic sites, especially the pirenzepine binding sites, on the other hand, suggest that the AF122 series may be particularly suited for the treatment of Alzheimer's disease.

TABLE 3

The effect of various putative cholinergic compounds on isolated guinea-pig ileum preparation.

| Compd. tested (#) | Lowest concn. ($\mu M$) | Intensity of contractions | Highest concn. ($\mu M$) | Intensity of contractions | Remarks |
|---|---|---|---|---|---|
| 4 | 8.0 | + | 33.0 | +++ | Blocked by atropine Full agonist |
| 5 | 3.3 | ++ | NT | | " |
| 6 | 3.3 | − | 6.6 | ++ | Blocked by atropine. |
| 8 | 1.7 | − | 50.0 | ++ | Blocked partially by atropine |
| 9 | NT | | 50.0 | − | Blocked contractions induced by ACh |
| 10 | 3.3 | +/− | 66.0 | ++ | Blocked partially by atropine |
| 11 | 3.3 | − | 1650.0 | − | At concn. of 330 $\mu M$ this compound reversibly blocked ACh-induced contractions |
| 12 | 3.3 | − | | | " |
| 13 | 6.6 | − | 1.3 | − | " |
| 14 | 3.3 | − | 66.0 | ++ | Blocked by atropine |

PHARMACODYNAMIC STUDIES

Material and Methods

Male white mice of the CD-1 strain supplied by Charles River Ltd. (U.K.) were used throughout. An acclimatization period of at least three days was allowed between arrival and commencement of a particular experimental series. The animals were fed a complete commercial pelleted rodent diet without restriction during the acclimatization and study periods. Animals had free access to tap water. Body weights during testing were mostly within 20–28 g.

Test materials were prepared as aqueous solutions in physiological saline (0.9% NaCl), up to a maximum concentration of 10 mg./ml. All materials were freshly prepared on the morning prior to each dosing session. Dosages were expressed gravimetrically (mg./kg.), in terms of the materials as received.

Groups of mice (mostly n=5) received either i.v. or oral administration of the test materials at various dose levels. Dose volumes appropriate for respective dose levels selected, were determined for each animal according to body weights on the day of dosing. Any behavioral changes occurring during one to two hours after administration, as well as incidence of death up to 24 hours after dosing were recorded.

Results

The effects of the test materials on the mice treated are presented in Table 4.

TABLE 4

Pharmacodynamic Profile and General Toxicity

| Compound | Dose mg/kg | Route | Mort.* No. | Time | Tre | Con | Res | Ana | Myd | Voc | Mot | Exo |
|---|---|---|---|---|---|---|---|---|---|---|---|---|
| (±)-III AF122A | 100 | i.v. | 2/2 | immed | | | | | | | | |
| | 50 | i.v. | 2/2 | 5 s | | 2/2 | | | | | | |
| | 25 | i.v. | 1/6 | 1 m | 3/6 | 1/6 | 4/6 | 4/5 | | 3/6 | | 3/6 |
| | 10 | i.v. | 0/5 | | | | | 2/5 | | 2/5 | | |
| | 200 | p.o. | 5/5 | 30 s | 5/5 | 5/5 | | | | | | |
| | 100 | p.o. | 0/5 | | 5/5 | | | | mod ♦ | | a | |
| | 50 | p.o. | 0/5 | | | | | | | | | |
| (+)-III AF122A | 100 | i.v. | 1/1 | immed | | | | | | | | |
| | 50 | i.v. | 4/5 | 30 s | 4/5 | 5/5 | | | | | | 3/5 |
| | 25 | i.v. | 0/5 | | | | | | mod | | a | |
| | 10 | i.v. | 0/5 | | | | | | | | | |
| | 200 | p.o. | 0/5 | | | | | | mod | | a+h | |
| | 100 | p.o. | 0/5 | | | | | | sl | | h | |
| | 50 | p.o. | 0/5 | | | | | | sl | | | |
| (−)-III AF122A | 100 | i.v. | 1/1 | immed | | | | | | | | |
| | 50 | i.v. | 1/1 | 10 s | 1/1 | 1/1 | | | | | | |
| | 25 | i.v. | 1/5 | 10 s | 4/5 | 1/5 | 4/5 | | | | h | 4/5 |
| | 10 | i.v. | 0/5 | | | | | | | | | |
| | 200 | p.o. | 1/5 | 10 m | 3/5 | 1/5 | 3/5 | | | 2/5 | h | |
| | 100 | p.o. | 0/5 | | | | | | | | h | |
| (±)-III AF122B | 100 | i.v. | 2/2 | immed | | | | | | | | |
| | 50 | i.v. | 2/2 | 5 s | 2/2 | 2/2 | | | | | | |
| | 25 | i.v. | 3/5 | | 5/5 | 5/5 | 2/5 | 2/5 | | | | 2/5 |
| | 10 | i.v. | 0/3 | | | | | | | | | |
| | 200 | p.o. | 4/4 | 15 m | 4/4 | 4/4 | 4/4 | 4/4 | | 2/4 | a | |
| | 100 | p.o. | 1/4 | 15 m | 4/4 | 4/4 | | 4/4 | | 1/4 | | |
| | 50 | p.o. | 0/5 | | | | | | | | | |
| (+)-III AF122B | 100 | i.v. | 2/2 | immed | | | | | | | | |
| | 50 | i.v. | 2/2 | 5 s | | | | | | | | |
| | 25 | i.v. | 4/5 | 30 s | 4/5 | 5/5 | 1/5 | | | | | |
| | 10 | i.v. | 1/8 | 5 s | 2/8 | 2/8 | 1/8 | 5/8 | | | | |
| | 200 | p.o. | 0/5 | | 3/5 | 5/5 | 4/5 | 5/5 | mod | 2/5 | a+h | |
| | 100 | p.o. | 0/5 | | | | 1/5 | 5/5 | sl | 1/4 | | |
| | 50 | p.o. | 0/5 | | | | | | | | | |
| (−)-III AF122B | 100 | i.v. | 2/2 | immed | | | | | | | | |
| | 50 | i.v. | 2/2 | 5 s | | 2/2 | | | | | | |
| | 25 | i.v. | 0/5 | | 3/5 | 3/5 | 2/5 | 5/5 | sl | 1/5 | a+h | |
| | 10 | i.v. | 0/5 | | | | | 3/5 | | | | |
| | 200 | p.o. | 4/4 | 20 m | 3/5 | 4/4 | 3/5 | 3/4 | mod | 2/4 | h | |
| | 100 | p.o. | 1/5 | | 1/5 | 2/5 | 1/5 | | mod | | h | |
| | 50 | p.o. | 0/5 | | | | | | sl | | a+h | |
| cis-II-sulfone | 100 | i.v. | 0/5 | | | | | 5/5 | mod | | h | |
| | 50 | i.v. | 0/5 | | | | | 3/5 | mod | | | |
| | 200 | p.o. | 0/5 | | | | | 5/5 | sl | | h | |
| | 100 | p.o. | 0/5 | | | | | | | | | |

*Mortality data includes No. dead/total treated, and Time in seconds (s) or minutes (m) after drug administration; immed = immediately.
**No. of animals affected/total no. treated
Tre = tremors;
Con = convulsive seizures, mostly of the clonic-tonic type;
Res = respiratory distress, mostly hyperpnoea and tachypnoea;
Ana = analgesia, indicated by non-responsiveness to tail pinch;
Myd = mydriasis: slight (sl) or moderate (mod)
(♦ Diarrhea also found to be moderate);
Voc = vocalization, i.e. repeated squeaking by unevoked animal;
Mot = altered motor activity, either hyperactivity and/or hyperreflectivity (a) or haunched posture (h)
Exo = exophthalmus

Conclusions

Within the toxic lethal range, all compounds tested exhibited a more or less similar sequence of central toxic effects, consisting mainly of tremor, clonic-tonic convulsions and respiratory irregularities. In case of intravenous administration, 100% mortality occurred at the dose level of 50 mg./kg., with the exception of cis-II-sulfone. On the basis of the mortality data from oral administration experiments, it appears that with respect to III (both AF122A and AF122B), the (+)-isomer is the less toxic in comparison with the racemate and the (−)-isomer.

BEHAVIORAL STUDIES

Development of potential drugs for the treatment of Alzheimer's disease requires their evaluation in appropriate animal models for this disease. Ethylcholine aziridinium (AF64A) induced cholinotoxicity mimics the cholinergic hypofunction reported in Alzheimer's disease and can be utilized as a workable animal model for this disorder (Fisher & Hanin, Ann. Rev. Pharmacol. 1986, 26: 161–181); AF64A (3 nmole/2 $\mu$l./side, icv) induces a cholinergic hypofunction confined mainly to the hippocampus. This hippocampal cholinergic deficiency is accompanied by statistically significant cognitive impairments (inter alia) in step-through passive avoidance (PA). The present PA experiment investigated the possibility of reversing such impairments by administration of (+)-III (AF122B).

31–41 weeks post-operation, the AF64A and saline-injected groups were randomly subdivided into two treatment sub-groups. Sub-group 1 was treated with 1 mg./kg. i.p. (+)-III (AF122B), while sub-group 2 was treated with 1 mg./kg. i.p. saline. The drug or saline were administered immediately after shock.

Initial latency and retention latency were analyzed by two-way ANOVA (Injection-AF64A/saline vs. (+)-III (AF122B)/saline. The results of both determinations are shown in Table 5. No significant differences were found during training, between any of the groups.

TABLE 5

| | Retention Latency (seconds) | |
|---|---|---|
| | Saline (1 mg./kg. i.p.) | (+)-III (AF122B) (1 mg./kg. i.p.) |
| AF64A | 202.1 ± 55.6 | 549.5 ± 29.1 |
| Saline | 584 ± 16 | 552 ± 33.7 |

The step-through latency of the AF64A-injected group was significantly shorter [F(1.53)=27.31; p<0.001] during the 72 hour retention test than the latency of the saline-injected group. In addition there was a general significant treatment effect [F(2.53)=9.66; p<0.001]. The interaction between Injection and Treatment was statistically significant [F(2.53)=14.51; p<0.001].

Shifee contrasts revealed that administration of (+)-III (AF122B) prolonged the retention latency of AF64A-injected rats (p<0.01) but had no significant effect on the retention latency of saline-injected rats. The results indicate that (+)-III (AF122B) treatment improved the passive avoidance retention of AF64A-injected rats.

While certain embodiments of the invention have been particularly described, it will be apparent to those skilled in the art that many modifications and variations may be made. The invention is accordingly not to be construed as restricted to such embodiments, rather its scope will be defined in accordance with the following claims.

We claim:
1. A compound of the formula (I)

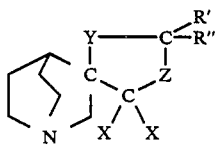

and geometrical isomers, enantiomers, diastereoisomers, racemates and acid addition salts thereof, wherein one of Y and Z is O and the other is $S(=O)_n$; n is 0, 1 or 2; R' and R" are each selected from the group consisting of hydrogen, lower alkyl, lower alkenyl, lower alkynyl, hydroxy lower alkyl, amino lower alkyl, $C_{3-7}$ cycloalkyl, phenyl, diphenyl methylol, and lower alkyl substituted by one or two phenyl groups, provided that at least R' or R" is other than hydrogen; and each X is hydrogen, or when Y is O and Z is $S(=O)_n$ simultaneously, then each X may also be selected from the group consisting of deuterium and tritium, and provided further that when each X is hydrogen, Y is O and Z is S simultaneously, then at least one of R' and R" is selected from the group consisting of lower alkenyl, lower alkynyl, cyclopropyl, cyclobutyl, cycloheptyl, hydroxy lower alkyl and amino lower alkyl.

2. A compound according to claim 1, wherein in formula (I), X is H, Y is O and Z is $S(=O)_n$; n is 0, 1 or 2; R' and R" are each selected from the group consisting of hydrogen, lower alkyl, lower alkenyl, lower alkynyl, hydroxy lower alkyl, amino lower alkyl, $C_{3-7}$ cycloalkyl, phenyl, diphenyl methylol, and lower alkyl substituted by one or two phenyl groups, provided that at least R' or R" is other than hydrogen, and that when Z is S, then at least one of R' and R" is selected from the group consisting of lower alkenyl, lower alkynyl, cyclopropyl, cyclobutyl, cycloheptyl, hydroxy lower alkyl and amino lower alkyl.

3. A compound according to claim 1, wherein in formula (I), X is selected from the group consisting of deuterium and tritium, Y is O and Z is $S(=O)_n$; n is 0, 1 or 2; and R' and R" are each selected from the group consisting of hydrogen, lower alkyl, lower alkenyl, lower alkynyl, hydroxy lower alkyl, amino lower alkyl, $C_{3-7}$ cycloalkyl, phenyl, diphenyl methylol, and lower alkyl substituted by one or two phenyl groups, provided that at least R' or R" is other than hydrogen.

4. A compound according to claim 1, wherein in formula (I), X is H, Z is O and Y is $S(=O)_n$; n is 0, 1 or 2; and R' and R" are each selected from the group consisting of hydrogen, lower alkyl, lower alkenyl, lower alkynyl, hydroxy lower alkyl, amino lower alkyl, $C_{3-7}$ cycloalkyl, phenyl, diphenyl methylol, and lower alkyl substituted by one or two phenyl groups, provided that at least R' or R" is other than hydrogen.

5. A compound according to claim 1, wherein in formula (I), X is H, Z is O and Y is $S(=O)_n$; n is 0, 1 or 2; one of R' and R" is hydrogen and the other of R' and R" is methyl.

6. A compound according to claim 1, wherein in formula (I), X is selected from the group consisting of deuterium and tritium, Y is O and Z is $S(=O)_n$; n is 0, 1 or 2; one of R' and R" is hydrogen and the other of R' and R" is methyl.

7. A compound according to claim 1, wherein formula (I) defines a compound selected from the group consisting of 2-methylspiro(1,3-oxathiolan-5,3')quinuclidine-3-oxide, 2-methylspiro(1,3-oxathiolan-5,3')quinuclidine-3,3-dioxide, 4,4-dideutero-2-methylspiro(1,3-oxathiolan-5,3')quinuclidine-3-oxide, 4,4-ditritio-2-methylspiro(1,3-oxathiolan-5,3')quinuclidine-3-oxide, 4,4-dideutero-2-methylspiro(1,3-oxathiolan-5,3')quinuclidine, 4,4-ditritio-2-methylspiro(1,3-oxathiolan-5,3')quinuclidine and 2-methylspiro(1,3-oxathiolan-4,3')quinuclidine.

8. A compound according to claim 7, which is selected from the group consisting of cis-2-methylspiro(1,3-oxathiolan-5,3')quinuclidine-cis-3-oxide, cis-2-methylspiro(1,3-oxathiolan-5,3')quinuclidine-trans-3-oxide, trans-2-methylspiro(1,3-oxathiolan-5,3')quinuclidine-cis-3-oxide, trans-2-methylspiro(1,3-oxathiolan-5,3')quinuclidine-trans-3-oxide, cis-2-methylspiro(1,3-oxathiolan-5,3')quinuclidine-3,3-dioxide, trans-2-methylspiro(1,3-oxathiolan-5,3')quinuclidine-3,3-dioxide, cis-4,4-dideutero-2-methylspiro(1,3-oxathiolan-5,3')quinuclidine-trans-3-oxide, cis-4,4-ditritio-2-methylspiro(1,3-oxathiolan-5,3')quinuclidine-trans-3-oxide, cis-4,4-dideutero-2-methylspiro(1,3-oxathiolan-5,3')quinuclidine, and cis-4,4-ditritio-2-methylspiro(1,3-oxathiolan-5,3')quinuclidine, and enantiomers, diastereoisomers, racemates and acid addition salts thereof, and (+)-cis-2-methylspiro(1,3-oxathiolan-4,3')quinuclidine, (+)-trans-2-methylspiro(1,3-oxathiolan-4,3')quinuclidine, (−)-cis-2-methylspiro(1,3-oxathiolan-4,3')quinuclidine, (−)-trans-2-methylspiro(1,3-oxathiolan-4,3')quinuclidine, (±)-cis-2-methylspiro(1,3-oxathiolan-4,3')quinuclidine and (±)-trans-2-methylspiro(1,3-oxathiolan-4,3')quinuclidine, and acid addition salts thereof.

9. A pharmaceutical composition for use in treating diseases of the central nervous system in mammals, which comprises an effective central nervous system treating amount of at least one member of the group consisting of compounds of the formula (I) as depicted in claim 1, and geometrical isomers, enantiomers, diastereoisomers and racemates thereof, wherein one of Y and Z is O and the other is $S(=O)_n$; n is 0, 1 or 2; R' and R" are each selected from the group consisting of hydrogen, lower alkyl, lower alkenyl, lower alkynyl, hydroxy lower alkyl, amino lower alkyl, $C_{3-7}$ cycloalkyl, phenyl, diphenyl methylol, and lower alkyl substituted by one or two phenyl groups, provided that at least R' or R" is other than hydrogen; and each X is hydrogen, or when Y is O and Z is $S(=O)_n$ simultaneously, then each X may also be selected from the group consisting of deuterium and tritium, and provided further that when each X is hydrogen, Y is O and Z is S simultaneously, then at least one of R' and R" is selected from the group consisting of lower alkenyl, lower alkynyl, cyclopropyl, cyclobutyl, cycloheptyl, hydroxy lower alkyl and amino lower alkyl, and pharmaceutically compatible acid addition salts thereof, together with an inert carrier or diluent.

10. A pharmaceutical composition according to claim 9, which is in a form suitable for oral, rectal, parenteral or transdermal administration, or for administration by insufflation or nasal spray.

11. A pharmaceutical composition according to claim 10, which is in a form suitable for transdermal administration and which comprises as an additional component, a low molecular weight fatty acid.

12. A pharmaceutical composition according to claim 11, which is in unit dosage form.

13. A pharmaceutical composition according to claim 12, wherein said at least one member or a pharmaceutically compatible acid addition salt thereof is present in an amount in the range of about 0.5 to about 100 mg., together with an inert carrier or diluent.

14. A pharmaceutical composition according to claim 13, wherein said amount lies within the range of about 5 to about 100 mg.

15. A pharmaceutical composition according to claim 14, wherein said amount lies within the range of about 10 to about 50 mg.

16. A pharmaceutical composition according to claim 9, herein said at least one member is selected from the group consisting of 2-methylspiro(1,3-oxathiolan-5,3')quinuclidine-3-oxide, 2-methylspiro(1,3-oxathiolan-5,3')quinuclidine-3,3-dioxide, 4,4-dideutero-2-methylspiro(1,3-oxathiolan-5,3')quinuclidine-3-oxide, 4,4-ditritio-2-methylspiro(1,3-oxathiolan-5,3')quinuclidine-3-oxide, 4,4-dideutero-2-methylspiro(1,3-oxathiolan-5,3')quinuclidine, 4,4-ditritio-2-methylspiro(1,3-oxathiolan-5,3')quinuclidine and 2-methylspiro(1,3-oxathiolan-4,3')quinuclidine, and enantiomers, diastereoisomers, racemates and pharmaceutically compatible acid addition salts thereof.

17. A pharmaceutical composition according to claim 16, wherein said at least one member is selected from the group consisting of cis-2-methylspiro(1,3-oxathiolan-5,3')quinuclidine-cis-3-oxide, cis-2-methylspiro(1,3-oxathiolan-5,3')quinuclidine-trans-3-oxide, trans-2-methylspiro(1,3-oxathiolan-5,3')quinuclidine-cis-3-oxide, trans-2-methylspiro(1,3-oxathiolan-5,3')quinuclidine-trans-3-oxide, cis-2-methylspiro(1,3-oxathiolan-5,3')quinuclidine-3,3-dioxide, trans-2-methylspiro(1,3-oxathiolan-5,3')quinuclidine-3,3-dioxide, cis-4,4-dideutero-2-methylspiro(1,3-oxathiolan-5,3')quinuclidine-trans-3-oxide, cis-4,4-ditritio-2-methylspiro(1,3-oxathiolan-5,3')quinuclidine-trans-3-oxide, cis-4,4-dideutero-2-methylspiro(1,3-oxathiolan-5,3')quinuclidine, and cis-4,4-ditritio-2-methylspiro(1,3-oxathiolan-5,3')quinuclidine, and enantiomers, diastereoisomers, racemates and pharmaceutically compatible acid addition salts thereof, and (+)-cis-2-methylspiro(1,3-oxathiolan-4,3')quinuclidine, (+)-trans-2-methylspiro(1,3-oxathiolan-4,3')quinuclidine, (−)-cis-2-methylspiro(1,3-oxathiolan-4,3')quinuclidine, (−)-trans-2-methylspiro(1,3-oxathiolan-4,3')quinuclidine, (±)-cis-2-methylspiro(1,3-oxathiolan-4,3')quinuclidine and (±)-trans-2-methylspiro(1,3-oxathiolan-4,3')quinuclidine, and pharmaceutically compatible acid addition salts thereof.

18. A pharmaceutical composition according to claim 17, which is in a form suitable for oral, rectal, parenteral or transdermal administration, or for administration by insufflation or nasal spray.

19. A pharmaceutical composition according to claim 18, which is in a form suitable for transdermal administration and which comprises as an additional component, a low molecular weight fatty acid.

20. A pharmaceutical composition for use in treating diseases of the central nervous system in mammals, which comprises:

(a) an effective central nervous system treating amount of at least one member of the group consisting of compounds of the formula (I) as depicted in claim 1, and geometrical isomers, enantiomers, diastereoisomers and racemates thereof, wherein one of Y and Z is O and the other is $S(=O)_n$; n is 0, 1 or 2; R' and R" are each selected from the group consisting of hydrogen, lower alkyl, lower alkenyl, lower alkynyl, hydroxy lower alkyl, amino lower alkyl, $C_{3-7}$ cycloalkyl, phenyl, diphenyl methylol, and lower alkyl substituted by one or two phenyl groups, provided that at least R' or R" is other than hydrogen; and each X is hydrogen, or when Y is O and Z is $S(=O)_n$ simultaneously, then each X may also be selected from the group consisting of deuterium and tritium, and (b) at least one compound selected from the group consisting of physostigmine, tetrahydroaminoacridine, choline, lecithin, piracetam, aniracetam, pramiracetam, oxiracetam, 4-aminopyridine, 3,4-diaminopyridine, somatostatin, pirenzepine, N-methylatropine, N-butylscopolamine, scopolamine, clonidine, quanfamicine and Nerve Growth Factor, and provided further that when each X is hydrogen, Y is O and Z is S simultaneously, then either in component (a) at least one of R' and R" is selected from the group consisting of lower alkenyl, lower alkynyl, cyclopropyl, cyclobutyl, cycloheptyl, hydroxy lower alkyl and amino lower alkyl, or component (b) comprises at least one compound selected from the group consisting of pirenzepine, N-methylatropine, N-butylscopolamine, scopolamine, clonidine, quanfamicine and Nerve Growth Factor.

21. A pharmaceutical composition according to claim 20 and which also comprises an inert carrier or diluent.

22. A pharmaceutical composition according to claim 21, which is in a form suitable for oral, rectal, parenteral or transdermal administration, or for administration by insufflation or nasal spray.

23. A pharmaceutical composition according to claim 22, wherein the form suitable for transdermal administration comprises as an additional component, a low molecular weight fatty acid.

24. A pharmaceutical composition for use in treating diseases of the central nervous system in mammals, which comprises:
  (a) an effective central nervous system treating amount of at least one member selected from the group consisting of 2-methylspiro(1,3-oxathiolan-5,3')quinuclidine-3-oxide, 2-methylspiro(1,3-oxathiolan-5,3')quinuclidine-3,3-dioxide, 4,4-dideutero-2-methylspiro(1,3-oxathiolan-5,3')quinuclidine-3-oxide, 4,4-ditritio-2-methylspiro(1,3-oxathiolan-5,3')quinuclidine-3-oxide, 4,4-dideutero-2-methylspiro(1,3-oxathiolan-5,3')quinuclidine, 4,4-ditritio-2-methylspiro(1,3-oxathiolan-5,3')quinuclidine and 2-methylspiro(1,3-oxathiolan-4,3')quinuclidine, and enantiomers, diastereoisomers, racemates and pharmaceutically compatible acid addition salts thereof, and
  (b) at least one compound selected from the group consisting of physostigmine, tetrahydroaminoacridine, choline, lecithin, piracetam, aniracetam, pramiracetam, oxiracetam, 4-aminopyridine, 3,4-diaminopyridine, somatostatin, pirenzepine, N-methylatropine, N-butylscopolamine, scopolamine, clonidine, quanfamicine and Nerve Growth Factor.

25. A pharmaceutical composition according to claim 24 and which also comprises an inert carrier or diluent.

26. A pharmaceutical composition according to claim 25, which is in a form suitable for oral, rectal, parenteral or transdermal administration, or for administration by insufflation or nasal spray.

27. A pharmaceutical composition according to claim 26, wherein the form suitable for transdermal administration comprises as an additional component, a low molecular weight fatty acid.

28. A pharmaceutical composition according to claim 24, wherein component (a) comprises at least one member selected from the group consisting of: cis-2-methylspiro(1,3-oxathiolan-5,3')quinuclidine-cis-3-oxide, cis-2-methylspiro(1,3-oxathiolan-5,3')quinuclidine-trans-3-oxide, trans-2-methylspiro(1,3-oxathiolan-5,3')quinuclidine-cis-3-oxide, trans-2-methylspiro(1,3-oxathiolan-5,3')quinuclidine-trans-3-oxide, cis-2-methylspiro(1,3-oxathiolan-5,3')quinuclidine-3,3-dioxide, trans-2-methylspiro(1,3-oxathiolan-5,3')quinuclidine-3,3-dioxide, cis-4,4-dideutero-2-methylspiro(1,3-oxathiolan-5,3')quinuclidine-trans-3-oxide, cis-4,4-ditritio-2-methylspiro(1,3-oxathiolan-5,3')quinuclidine-trans-3-oxide, cis-4,4-dideutero-2-methylspiro(1,3-oxathiolan-5,3')quinuclidine, and cis-4,4-ditritio-2-methylspiro(1,3-oxathiolan-5,3')quinuclidine, and enantiomers, diastereoisomers, racemates and pharmaceutically compatible acid addition salts thereof, and (+)-cis-2-methylspiro(1,3-oxathiolan-4,3')quinuclidine, (+)-trans-2-methylspiro(1,3-oxathiolan-4,3')quinuclidine, (−)-cis-2-methylspiro(1,3-oxathiolan-4,3')quinuclidine, (−)-trans-2-methylspiro(1,3-oxathiolan-4,3')quinuclidine, (±)-cis-2-methylspiro(1,3-oxathiolan-4,3')quinuclidine and (±)-trans-2-methylspiro(1,3-oxathiolan-4,3')quinuclidine, and pharmaceutically compatible acid addition salts thereof.

29. A pharmaceutical composition according to claim 28 and which also comprises an inert carrier or diluent.

30. A pharmaceutical composition according to claim 29, which is in a form suitable for oral, rectal, parenteral or transdermal administration, or for administration by insufflation or nasal spray.

31. A pharmaceutical composition according to claim 30, wherein the form suitable for transdermal administration comprises as an additional component, a low molecular weight fatty acid.

32. A method for treating diseases of the central nervous system in mammals, which comprises administering to the mammal an effective central nervous system treating amount of at least one member of the group consisting of compounds of the formula (I) as depicted in claim 1, and geometrical isomers, enantiomers, diastereoisomers and racemates thereof, wherein one of Y and Z is O and the other is $S(=O)_n$; n is 0, 1 or 2; R' and R'' are each selected from the group consisting of hydrogen, lower alkyl, lower alkenyl, lower alkynyl, hydroxy lower alkyl, amino lower alkyl, $C_{3-7}$ cycloalkyl, phenyl, di phenylmethylol, and lower alkyl substituted by one or two groups, provided that at least R' or R'' is other than hydrogen; and each X is hydrogen, or when Y is O and Z is $S(=O)_n$ simultaneously, then each X may also be deuterium, and provided further that when each X is hydrogen, Y is O and Z is S simultaneously, then at least one of R' and R'' is selected from the group consisting of lower alkenyl, lower alkynyl, cyclopropyl, cyclobutyl, cycloheptyl, hydroxy lower alkyl and amino lower alkyl, and pharmaceutically compatible acid addition salts thereof.

33. A method as in claim 32, wherein said at least one member is administered in the form of a pharmaceutical composition according to any one of claims 9–31.

34. A method as in claim 32, wherein one of R' and R'' is methyl and the other is hydrogen.

35. A method as in claim 34, wherein there are treated diseases due to a deficiency in the central cholinergic system.

36. A method as in claim 34, wherein there is treated senile dementia of Alzheimer's type.

37. A method as in claim 36, wherein said at least one member is administered via the oral route in an amount which lies within the range of about 0.1 to about 60 mg./kg. body weight.

38. A method as in claim 37, wherein said amount lies within the range of about 0.1 to about 10 mg./kg. body weight.

39. A method as in claim 38 wherein said amount lies within the range of about 1 to about 5 mg./kg. body weight.

40. A method as in claim 36, wherein there is also coadministered with the said quinuclidine, at least one compound selected from the group consisting of physostigmine, tetrahydroaminoacridine, choline, lecithin, piracetam, aniracetam, pramiracetam, oxiracetam, 4-aminopyridine, 3,4-diaminopyridine, somatostatin, pirenzepine, N-methylatropine, N-butylscopolamine, scopolamine, clonidine, quanfamicine and Nerve Growth Factor, provided additionally that when said at least one compound is selected from the group consisting of pirenzepine, N-methylatropine, N-butylscopolamine, scopolamine, clonidine, quanfamicine and Nerve Growth Factor, then the restriction that when each X is hydrogen, Y is O and Z is S simultaneously, at least one of R' and R'' is necessarily selected from the group consisting of lower alkenyl, lower alkynyl, cyclopropyl, cyclobutyl, cycloheptyl, hydroxy lower alkyl and amino lower alkyl, does not apply.

41. A method as in claim 36, wherein said at least one member is administered via the parenteral route in an amount which lies within the range of about 0.01 to about 10 mg./kg. body weight.

42. A method as in claim 41, wherein said amount lies within the range of about 0.05 to about 5 mg./kg. body weight.

43. A method according to claim 42 wherein said amount lies within the range of about 0.1 to about 2 mg./kg. body weight.

* * * * *